US012728007B2

(12) United States Patent
Williams et al.

(10) Patent No.: US 12,728,007 B2
(45) Date of Patent: Sep. 8, 2026

(54) BONE CAP

(71) Applicant: University of Utah Research Foundation, Salt Lake City, UT (US)

(72) Inventors: Dustin L Williams, Salt Lake City, UT (US); Richard Tyler Epperson, Salt Lake City, UT (US); Brad M. Isaacson, Salt Lake City, UT (US); Brooke Kawaguchi, Salt Lake City, UT (US); Mary Grace Canapi, Salt Lake City, UT (US)

(73) Assignee: University of Utah Research Foundation, Salt Lake City, UT (US)

(*) Notice: Subject to any disclaimer, the term of this patent is extended or adjusted under 35 U.S.C. 154(b) by 628 days.

(21) Appl. No.: 18/252,467

(22) PCT Filed: Nov. 11, 2021

(86) PCT No.: PCT/US2021/058970
§ 371 (c)(1),
(2) Date: May 10, 2023

(87) PCT Pub. No.: WO2022/103953
PCT Pub. Date: May 19, 2022

(65) Prior Publication Data

US 2024/0000572 A1 Jan. 4, 2024

Related U.S. Application Data

(60) Provisional application No. 63/112,468, filed on Nov. 11, 2020.

(51) Int. Cl.

| | |
|---|---|
| ***A61F 2/28*** | (2006.01) |
| *A61F 2/30* | (2006.01) |
| *A61F 2/78* | (2006.01) |

(52) U.S. Cl.
CPC .. *A61F 2/2814* (2013.01); *A61F 2002/30589* (2013.01); *A61F 2002/30843* (2013.01);
(Continued)

(58) Field of Classification Search
CPC .. A61F 2/28; A61F 2/2814; A61F 2002/7887; A61F 2/30767; A61F 2/78;
(Continued)

(56) References Cited

U.S. PATENT DOCUMENTS

| | | | |
|---|---|---|---|
| 3,906,550 | A | 9/1975 | Rostoker et al. |
| 4,447,915 | A | 5/1984 | Weber |

(Continued)

FOREIGN PATENT DOCUMENTS

| | | | |
|---|---|---|---|
| DE | 9317395 | U1 | 1/1994 |
| FR | 2776917 | A1 | 10/1999 |

(Continued)

OTHER PUBLICATIONS

Anugraha et al., "End-capping of amputation stumps with a local antibiotic containing hydroxyapatite bio-composite—A report of 13 cases with chronic lower limb osteomyelitis", *Journal of Orthopaedics*, vol. 17, (Jan.-Feb. 2020), pp. 124-126, https://doi.org/10.1016/j.jor.2019.11.007.

(Continued)

*Primary Examiner* — Vi X Nguyen
(74) *Attorney, Agent, or Firm* — Thorpe North & Western, LLP; Erik S. Ericksen

(57) ABSTRACT

A bone cap (100) for preventing leakage of medullary canal components in a residual limb (102) that can lead to pathologies such as heterotopic ossification reducing heterotopic ossification and a method for using the same are provided. The bone cap (100) includes a proximal base (114) and an insertion extension portion (116) extending from the proximal base (114). The insertion extension portion (116) has an
(Continued)

outer surface and a distal end (112*b*) opposite the proximal base (114). The insertion extension portion (116) is configured to be inserted into a resected portion of a bone (104) of a patient. The bone cap (100) also has at least one bone engaging feature (120) disposed on the outer surface of the insertion extension portion (116) adjacent to the distal end (112*b*) of the insertion extension portion (116). A porous coating (122) is disposed on the outer surface of the insertion extension portion (116) adjacent to the proximal base (114).

19 Claims, 5 Drawing Sheets

(52) U.S. Cl.
CPC ............... *A61F 2002/30881* (2013.01); *A61F 2002/7887* (2013.01)

(58) Field of Classification Search
CPC .. A61F 2002/30067; A61F 2002/30224; A61F 2002/30677
See application file for complete search history.

(56) References Cited

U.S. PATENT DOCUMENTS 4,950,295 A 8/1990 Weigum et al.
5,405,388 A 4/1995 Fox
5,782,917 A 7/1998 Carn
6,251,141 B1 6/2001 Pierson, III et al.
6,669,733 B1 12/2003 Spierings
7,608,110 B2 * 10/2009 O'Driscoll ............ A61F 2/4684 623/20.11
8,444,701 B2 5/2013 Bloebaum et al.
8,545,560 B2 10/2013 Malawer
9,440,009 B2 9/2016 Armbruster et al.
9,510,876 B2 12/2016 Appenzeller et al.
10,610,365 B2 * 4/2020 Librot ....................... A61F 2/36
2006/0142772 A1 6/2006 Ralph et al.
2011/0082561 A1 4/2011 Forrester
2015/0025650 A1 * 1/2015 Nutter .................. A61F 2/2814 623/23.48
2019/0083266 A1 3/2019 Cook et al.
2019/0240030 A1 8/2019 Coulange et al.
2020/0022742 A1 1/2020 Li et al.
2020/0113700 A1 4/2020 Ogawa
2021/0030548 A1 2/2021 Cutler

FOREIGN PATENT DOCUMENTS

WO 2014040061 3/2014
WO 2018208913 11/2018

OTHER PUBLICATIONS

International Search Report for Serial No. PCT/US2021/058970 dated Jan. 6, 2022, 12 pages.
Extended European Search Report for European Patent Application No. 21892804.2-1122 / 4243737 PCT/US2021058970, Applicant University of Utah Research Foundation, dated Jul. 9, 2024, 7 pages.

* cited by examiner

BONE CAP

RELATED APPLICATION

This application claims priority to U.S. Provisional Application No. 63/112,468 which was filed on Nov. 11, 2020, the contents of which are hereby incorporated by reference in their entirety.

GOVERNMENT INTEREST

This invention was funded by The United States as represented by the Department of Veterans Affairs (Washington, D.C.).

BACKGROUND

Heterotopic ossification (HO) is the abnormal growth of extra skeletal bone in muscle, tendons, and/or other soft tissue. HO can occur as a result of either local or neurological trauma or as a genetic disorder. It is often seen in a variety of conditions such as amputations, orthopedic surgery, bone fracture or dislocation, traumatic brain and spinal cord injury, and severe burns. In post-traumatic amputations, the incidence of HO is relatively high with an occurrence in approximately 65% of combat-injured patients. However, some estimates place the incidence of HO in severe traumatic amputations at above 90%. Unfortunately, causes of HO are not well understood. But in general, it is thought to be the result of an influx of inflammatory cells on a tissue injury which causes abnormal formation of bone. In limb amputations, HO can result in pain and skin breakdown while adversely impacting both the fit and use of prosthetics for the patient. First line treatment of HO involves adjusting the prosthetic and treating with non-steroidal anti-inflammatory drugs or local radiation therapy. If these treatments are unsuccessful, surgical excision of the abnormal bone growth is performed and required in about 20-40% of cases.

Capping the end of a bone has been shown to minimize bone overgrowth. This trend has resulted in increased research in this area with a focus on novel capping materials and procedures, however, the link with HO is not definitive. Nonetheless, stump capping of amputated limbs has been discussed in the literature since the 1960s and 1970s. Typically, these studies have focused on children, as amputations in children often result in the stump extending. Studies have been performed on capping procedures using different materials, however, there is a high revision rate due to failure of fixation, infection, issues with the soft tissue covering, and fracture.

Management of HO in limb amputees is also focusing on osseointegration. This is a surgical procedure that fixes a metal bar into the remaining bone, which extends out of the skin to act as a dock for the prosthetic. A prosthetic can then be easily and cleanly attached to the dock. This type of docking system provides greater pain relief while mitigating any pain due to HO, as the soft tissue socket is no longer compressed against HO in the region.

It is estimated that there are nearly 2 million Americans living with limb loss. By 2050, this number is expected to double. With HO as a known complication of amputation, there is a need to better understand the HO process and ways to mitigate its incidence.

SUMMARY

Accordingly, the disclosed embodiments relate to a bone cap and a method of bone capping that can mitigate incidence of HO specifically in amputees. A bone cap for reducing leakage of medullary canal components in a residual limb that can lead to pathologies such as heterotopic ossification is provided. The bone cap can include a proximal base and an insertion extension portion extending from the proximal base. The insertion extension portion can have an outer surface and a distal end opposite the proximal base. The insertion extension portion can be configured to be inserted into a resected portion of a bone of a patient.

The bone cap can further include at least one bone engaging feature that is disposed on the outer surface of the insertion extension portion. The bone engaging feature can be located adjacent to the distal end of the insertion extension portion. A porous coating can be disposed on the outer surface of the insertion extension portion adjacent to the proximal base.

A complementary method can include resecting an end of the bone of a patient to form a resection. The bone cap can then be inserted into the resection.

There has thus been outlined, rather broadly, features of the disclosed embodiments so that the detailed description thereof that follows may be better understood, and so that the present contribution to the art may be better appreciated. Other features of disclosed herein will become clearer from the following detailed description, taken with the accompanying drawings and claims, or may be learned by the practice of the disclosure.

Figure 1:
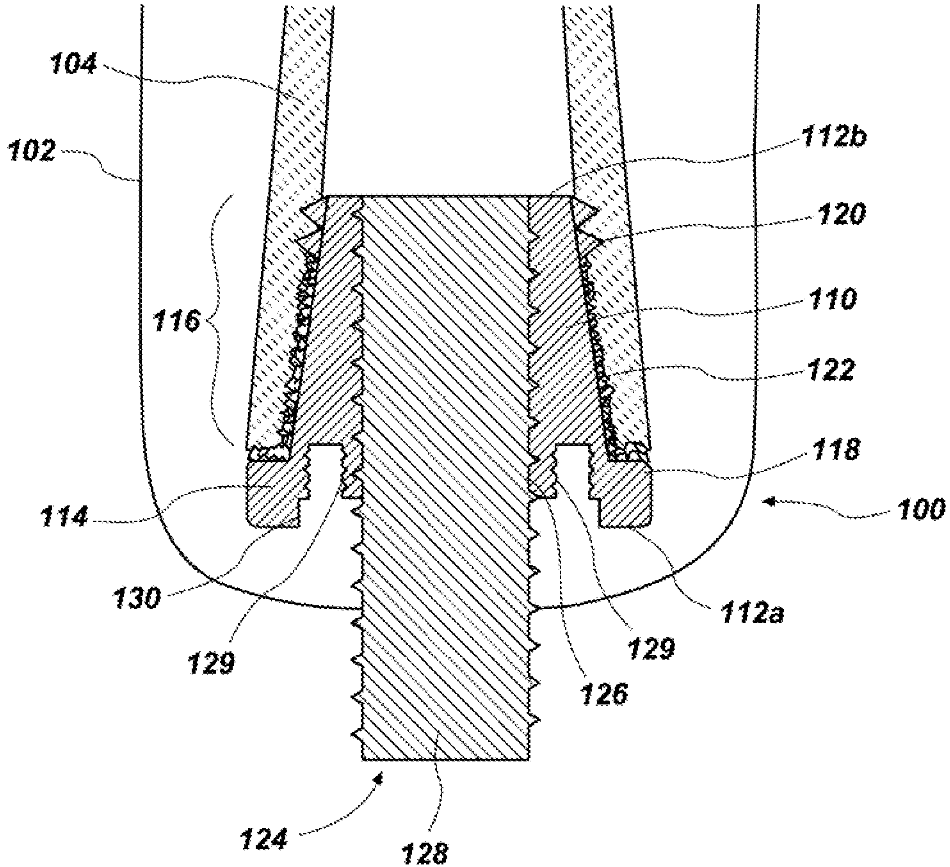
FIG. 1 is a cross-sectional view of a bone cap in accordance with an exemplary embodiment.

These drawings are provided to illustrate various aspects of the invention and are not intended to be limiting of the scope in terms of dimensions, materials, configurations, arrangements or proportions unless otherwise limited by the claims.

DETAILED DESCRIPTION

While these exemplary embodiments are described in sufficient detail to enable those skilled in the art to practice the disclosed subject matter, it should be understood that other embodiments may be realized and that various changes may be made without departing from the spirit and scope of the present invention. Thus, the following more detailed description of the embodiments is not intended to limit the scope of the invention, but is presented for purposes of illustration only to sufficiently enable one skilled in the art to practice the disclosed subject matter. Accordingly, the scope of the present invention is to be defined solely by the appended claims.

Definitions

In description and claims presented herein, the following terminology will be used.

The singular forms "a," "an," and "the" include plural referents unless the context clearly dictates otherwise. Thus, for example, reference to "a protrusion" includes reference to one or more of such features and reference to "the bone cap" refers to one or more of such devices.

As used herein with respect to an identified property or circumstance, "substantially" refers to a degree of deviation that is sufficiently small so as to not measurably detract from the identified property or circumstance. The exact degree of deviation allowable may in some cases depend on the specific context.

As used herein, "adjacent" refers to the proximity of two structures or elements. Particularly, elements that are identified as being "adjacent" may be either abutting or connected. Such elements may also be near or close to each other without necessarily contacting each other. The exact degree of proximity may in some cases depend on the specific context.

As used herein, the term "about" is used to provide flexibility and imprecision associated with a given term, metric or value. The degree of flexibility for a particular variable can be readily determined by one skilled in the art. However, unless otherwise enunciated, the term "about" generally connotes flexibility of less than 2%, and most often less than 1%, and in some cases less than 0.01%.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

As used herein, the term "at least one of" is intended to be synonymous with "one or more of." For example, "at least one of A, B and C" explicitly includes only A, only B, only C, or combinations of each.

Numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a numerical range of about 1 to about 4.5 should be interpreted to include not only the explicitly recited limits of 1 to about 4.5, but also to include individual numerals such as 2, 3, 4, and sub-ranges such as 1 to 3, 2 to 4, etc. The same principle applies to ranges reciting only one numerical value, such as "less than about 4.5," which should be interpreted to include all of the above-recited values and ranges. Further, such an interpretation should apply regardless of the breadth of the range or the characteristic being described.

Any steps recited in any method or process claims may be executed in any order and are not limited to the order presented in the claims. Means-plus-function or step-plus-function limitations will only be employed where for a specific claim limitation all of the following conditions are present in that limitation: a) "means for" or "step for" is expressly recited; and b) a corresponding function is expressly recited. The structure, material or acts that support the means-plus function are expressly recited in the description herein. Accordingly, the scope of the invention should be determined solely by the appended claims and their legal equivalents, rather than by the descriptions and examples given herein.

Bone Caps

In the embodiments disclosed below, a bone cap device and method to cap bones to attempt to better prevent HO is provided. The disclosed embodiments relate to a bone cap and a method of bone capping that can mitigate incidence of HO specifically in amputees.

Exemplary embodiments can include a bone cap device that can plug into the medullary canal of an amputated limb or serve as a prosthetic dock. The bone cap can have pyramid shaped protrusions (e.g. teeth) to allow for an intimate scratch-fit inside the bone sufficient to at least temporarily secure and fix the bone cap device relative to the bone. Such secure fitment can allow for initial fixation at the time of surgery. Secondary fixation of the bone cap can be facilitated through a cementless coating that allows for bone growth/remodeling and skeletal attachment. In another embodiment, a cemented version lacking a porous coating can also be used with standard or antimicrobial polymethyl methacrylate (PMMA) bone cement in patients with compromised bone stock (e.g. osteoporosis).

One exemplary embodiment of a bone cap can include a solid component with a rounded, smooth, exposed surface that can articulate freely around the surrounding tissue. This component would serve as a long-term device without the need for any revision surgery. This bone cap can employ advancements in material and, with the addition of the protrusions, can allow for a better fit to the bone to prevent leakage of cells from the medullary canal which can contribute to HO.

Another exemplary embodiment can include a bone cap that is configured to be used as a prosthetic dock. In this embodiment, there can be an interchangeable component that allows for different surfaces to be attached at the end of the cap. This allows various articulating surfaces and/or antimicrobial inserts to be attached to the cap. The component can be hollow, thereby providing insertion of a rod/stem into the medullary canal to support a prosthetic limb or digit. Alternatively, the end of the cap can have an integrated attachment feature which allows direct attachment of the prosthetic. For example, such attachment features can include, but are not limited to, a hollow receiver opening, stem, hook, latch, pin, screw, or the like. Prosthetics can include functional attachments, aesthetic attachments, etc. such as, but not limited to, replacement limbs, hooks, other tools, and the like.

Figure 2:
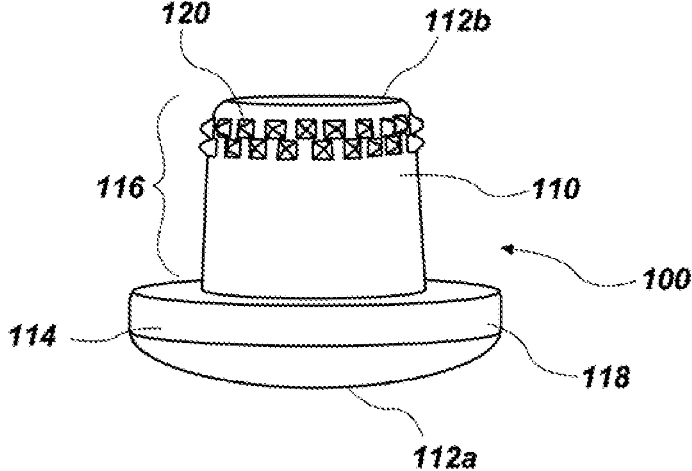
FIG. 2 is a front perspective view of the bone cap of FIG. 1.
Figure 3:
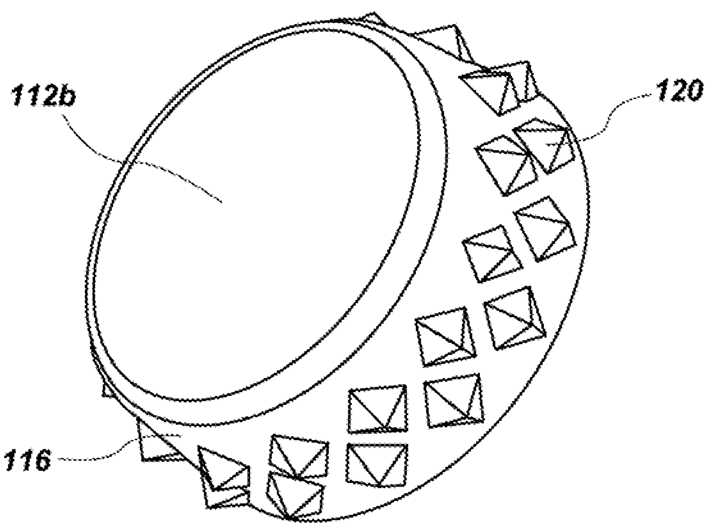
FIG. 3 is an exemplary distal end of a bone cap.

FIG. 1 illustrates a cross-sectional view of a bone cap 100 in accordance with an exemplary embodiment. FIG. 2 illustrates a front perspective view of the bone cap of FIG. 1. FIG. 3 illustrates an exemplary distal end of a bone cap. As shown in FIGS. 1-3, a bone cap 100 for reducing leakage of medullary canal components in a residual limb 102 that can lead to pathologies such as HO is provided. The bone cap 100 can be configured as a permanent plug or can be configured as a dock to which a prosthetic and/or antimicrobial inserts can be attached. The bone cap 100 can aid in reducing HO.

The bone cap 100 can comprise a body 110 having a proximal end 112*a* and a distal end 112*b*. The body 110 can comprise a proximal base 114 located at a proximal end of the body 110 and an insertion extension portion 116 extending from the proximal base 114 and terminating at the distal end 112*b* opposite the proximal base 114. The insertion extension portion 116 can be configured to be inserted into a resected portion of a bone 104 of a patient. The bone cap 100 can further comprise at least one bone engaging protrusion 120 that is disposed on the outer surface of the insertion extension portion 116. In the example shown in FIGS. 1-3, the bone engaging protrusions 120 are disposed adjacent to the distal end 112*b* of the insertion extension portion 116.

The bone cap 100 can be formed from suitable biocompatible materials. Such materials can include metallic materials such as titanium or can also include biocompatible polymers or ceramics. In one example, the bone cap can be formed of a metallic material. Other non-limiting examples of suitable biocompatible materials can include stainless steel, titanium, Ti-6Al-7Nb, alumina, zirconia, bioglass, hydroxyapatite reinforced HDPE, polyether ether ketone (PEEK), alloys thereof, composites thereof, combinations thereof, and the like.

In some embodiments, the proximal base 114, insertion extension portion 116, and bone engaging protrusions 120 can be formed as a single, unitary piece. In other embodiments, these can be formed separately and can be joined together with fasteners, threading, adhesives, welding, or by another joining operation. Any suitable manufacturing process can be used, such as casting, forging, molding, 3D printing, etc. Additional processing can include machine finishing, milling, surface treatments (anodizing, polishing, coatings, etc), and the like.

In some embodiments, as shown in FIGS. 1-3, the insertion extension portion 116 can be formed in a frustoconical shaped structure that extends from the proximal base 114 to the distal end 112*b* of the insertion extension portion 116. The degree of taper can generally be very low, and can be generally less than about a 20%, and often less than about a 10%, decrease in width from the proximal base 114 to the distal end 112*b*. In other examples, the insertion extension portion 116 can be cylindrical. Regardless, in any of these iterations, the proximal base 114 can comprise an annular flange 118 extending about the proximal end 112*a* of the bone cap 100. The annular flange can provide a stop interface where a back perimeter side of the flange contacts an exposed end of the bone 104. This interface can provide a mechanical stop to control depth during insertion, as well as to provide additional support to future longitudinal weight bearing in conjunction with a longitudinal interface produced by the protrusions and porous coating described in more detail below. Thus, the stop interface provides support generally perpendicular to a direction of force between the device and bone, while the longitudinal interface provides shear support in a direction generally parallel to such force.

The insertion extension portion 116 can be appropriately sized to allow entry into the resected portion of the bone B while minimizing gaps and balancing width and length. Although specific dimensions can vary, an extension length to an extension distal width ratio can range from 2:1 to 0.5:1. However, a more compacted insertion extension portion 116 can provide a higher contact surface area with an interior surface of the bone. As such, the extension length to extension distal width ratio can often range from about 1.2 to 0.8:1. The size of the bone plug 100 can also be varied based on the particular patient and inner diameters of the corresponding bone canal. However, as a general rule, distal end widths of the insertion extension portion 116 can range from about 12 mm to about 25 mm, although other ranges may be used.

The bone engaging features can be protrusions, cavities, or can include combinations of both. The bone engaging protrusions 120 can be configured to act as teeth to allow for a snug and secure scratch-fit inside the bone 104. Providing a tight fit can be sufficient to allow for initial fixation of the bone cap 100 within a resected portion of the bone 104 at the time of surgery. Thus, the bone engaging protrusions 120 can be formed to culminate in a sharp point or edge. In some embodiments, the bone engaging protrusions 120 can be formed in a pyramid shape, such as those shown in FIGS. 1-3. The pyramid shape can extend outward and away from the outer surface of the insertion extension portion 116. Other shapes can include angular shapes such as, but not limited to, a conical shape, a wedge shape, a flange (regular or angled), a barbed component, fluted ribs, or the like. In some cases, the shapes can be rounded shapes such as, but not limited to, semispheres, elliptical humps, rounded ridges, rounded wedges, rounded wedges with an angled trailing upper end (e.g. ramps with a raised end oriented toward the distal end), and the like.

When the bone engaging features are cavities, the cavities can be coated with bone ingrowth material, porous coating, or other additives such as those disclosed herein. The cavities can be a recess having any suitable shape, e.g. concave semisphere, diamond recesses, and the like. The cavities can be sized and oriented in a similar matter to sizes, shapes, and patterns as described with respect to the protrusions. Furthermore, a mixture of protrusions and cavities can allow for both immediate bone engagement and bone engagement through ingrowth into the cavities over time.

In some embodiments, a plurality of bone engaging protrusions 120 can be disposed on the outer surface of the insertion extension portion 116. For example, the plurality of bone engaging protrusions 120 may be formed in an annular array adjacent to the distal end 112*b* of the insertion extension portion 116. In some embodiments, multiple rows or annular arrays of bone engaging protrusions 120 can be formed on the insertion extension portion 116. The engaging protrusions 120 in each row or annular array can be offset from those in adjacent rows to further enhance the ability of the engaging protrusions 120 to create an initial fixation inside the bone 104. Other patterns of bone engagement features can also be used. For example, engagement features can be arranged in a helical spiral pattern along the outer surface.

The bone cap 100 can further comprise a porous coating 122 disposed on the outer surface of the insertion extension portion 116. The porous coating 122 can extend along the insertion extension portion 116 from the proximal base 114 to the engaging protrusions 120. The porous coating 122 can be a cementless coating that allows for bone growth/remodeling and skeletal attachment. In some embodiments, the porous coating 122 can comprise a titanium porous coating known under the tradename "$P^2$" offered by DJO Surgical®. Other non-limiting examples of porous coatings can include bone scaffold films formed of bioceramics, PCL polymer, calcium phosphate, PEDOT:PSS, asymmetric spherical beads, lattice structures, K coatings, plasma spray coatings, porous foam titanium, porous cobalt chrome coatings, porous tantalum, combinations thereof containing multilayered coatings per ASTM standards, and the like. In some examples, the porous coating can include additives such as bone growth factors (e.g. platelet-derived growth factor (PDGF), bone morphogenetic protein 2(BMP-2), etc), osteogenic precursor cells, anti-inflammatory agents, antibiotics, antioxidants, antimicrobials, anesthetics, combinations thereof, or the like. For example, additives can be coated directly on the porous media or scaffold, and/or can be impregnated in a biodegradable polymer matrix disposed within the porous media. Non-limiting examples of suitable biodegradable polymer can include collagen, chitosan, PGA, PLA, PLLA, PLGA, PCL, TCP, hydroxyapatite, PBS, PPDO, polycarbonates, polyamides, combinations thereof, composites thereof, copolymers thereof, and the like.

In some examples, the porous coating 122 can be disposed on the back side of the annular flange 118 adjacent to the insertion extension portion 116. The porous coating 122 can be disposed on the insertion extension portion 116 adjacent to the proximal base 118 such that the porous coating 122 extends continuously from the annular flange 118 onto the insertion extension portion 116.

Furthermore, additional coating materials can be used on external surfaces of the bone cap 100. For example, the outer surface can be coated with a supplemental coating of one or more of growth factors to promote healing, antimicrobial coatings to enhance infection prevention, bone chips, a gel comprised of bioabsorbable hydrogel (e.g., Novagenit's defensive antimicrobial coating (DAC)) or a paste (e.g. cement) to be applied to minimize micromotion, etc. As one example, a paste can include PMMA with bisphosphonates to promote healing an reduce bone loss.

In this example, the bone engaging protrusions 120 can be located only at or near the distal end 112*b*. Thus, an intermediate region of the insertion extension portion 116 between the proximal base 114 and the engaging protrusions 120 comprises an outer surface that is free from the bone engaging protrusions 120. Although the proportion can vary, the bone engaging protrusions 120 can occupy from 2% to 50% of a distalmost portion of the outer surface of the insertion extension portion 116, and in some cases from 5% to 30%. In some examples, the porous coating can cover the entirety of, or at least a portion of, the intermediate region of the insertion extension portion 116 that is free from the bone engaging protrusions 120.

In some embodiments, the bone cap 100 can be formed as a permanent plug member having a smooth outer surface. In such cases, skin and other tissue can be allowed to grow over and cover the bone cap. In other embodiments, the bone cap 100 can be formed as a docking member to which other parts such as prosthetics or antimicrobial inserts may be attached. In this case at least a portion of the bone cap or prosthetics attached to the bone cap are exposed outside of the skin. To facilitate the attachment of such other parts, an attachment site 124 can be provided at a proximal end 112*a* of the bone cap 100. The attachment site 124 can comprise one or more apertures formed in the proximal base 114. For example, a central bore 126 can be formed in the bone cap 100 which can extend from the proximal end 112*a* at least partially through the length of the body 110 of the bone cap 100 towards the distal end 112*b*. In some examples, the central bore 126 can extend completely through the bone cap body 110 from the proximal end 112*a* to the distal end 112*b* (as illustrated). However, in other examples, the central bore can extend through only a portion of the bone cap body (e.g. leaving no direct fluid communication with intramedullary space).

The central bore 126 can be configured to accommodate one or more inserts 128, such as prosthetic attachments or antimicrobial inserts. In some examples, the insert 128 can comprise a removable bolt that can be threaded or otherwise secured into the central bore 126 to prevent migration of fluids into and out of the bone interior. The attachment site 124 can further comprise one or more threaded screw holes 129 to help secure parts to be attached to the bone cap 100 at the attachment site 124. The screw holes 129 can be disposed in any desired pattern to facilitate attachment of the one or more inserts 128 depending on the particular device to be attached. In some examples, the attachment site 124 can be formed in an annular recess 130 formed into the proximal end 112*a* the proximal base 114 to further stabilize parts to be attached to the bone cap 100.

Figure 4:
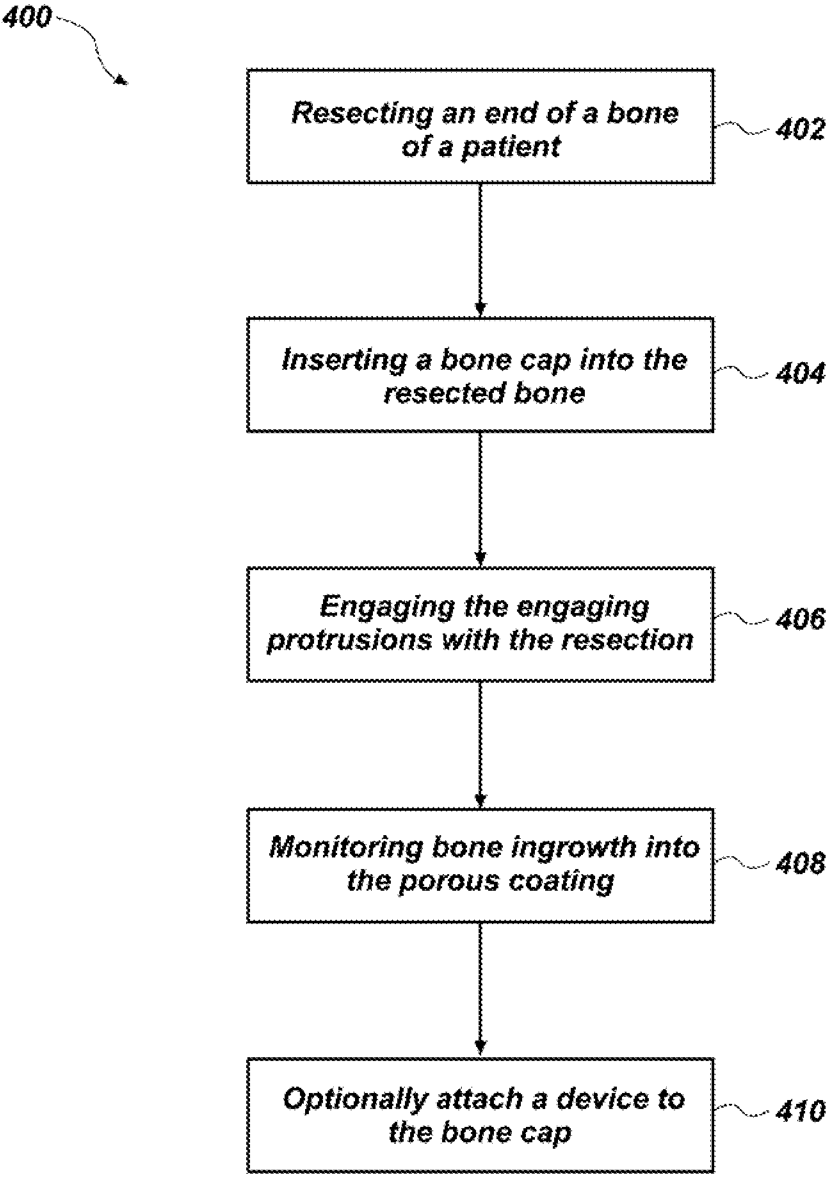
FIG. 4 illustrates a method of installing a bone cap into a bone of a patient.

FIG. 4 illustrates a method of installing a bone cap into a bone of a patient. The method 400 can be implemented using use the above-described bone cap 100 shown in FIGS. 1-3. In a first step 402, the method comprises the step of resecting an end of the bone 104 of the patient to facilitate the installation of the bone cap 100. The medullary canal of bone varies from patient to patient. In one optional example, to accommodate variations in canal width or length, 3D-printed or similar bone cap templates with varying sizes can be used to predetermine a proper bone cap size for a particular patient. The template can be slipped into the canal to confirm proper fit and fill, as well as diameter of the distal portion 112*a* of the bone cap. Once the desired size is determined, a bone cap matching that size can be selected for implantation. In another optional step, a calcar planar or similar device can be used to flatten and plane the bone to ensure the bone cap seats uniformly on the cross section of amputated bone. Then, in step 404, the bone cap is inserted into the resection. Specifically, the insertion extension portion 116 extending from the proximal base 114 is inserted into the medullary canal. In step 406, the bone engaging protrusions 120 are engaged with the inside of the medullary canal to facilitate initial attachment of the bone cap 100 to the bone 104 to securely lodge the cone cap within the resection. Optionally, the bone cap can then be mechanically driven into place using a concave hammer or similar device commonly used in orthopedics to abut the landing region 118 of the bone cap to the resected bone. The surrounding tissue would then be sutured and secured using standard surgical procedure and follow up performed every two to three months with, for example, radiography to assess placement and performance.

With the bone cap installed, the porous coating facilitates ingrowth and a permanent fixation within the bone. The patient can thus be monitored in step 408 to ensure proper bone growth and a stable connection between the bone and the bone cap. Further, the patient can be monitored for heterotopic ossification.

In some examples, the bone cap 100 can have an attachment site 124 as described above to facilitate attachment of a prosthetic or other device. With the bone cap 100 installed, the prosthetic can be installed via the attachment site 124 in step 410, such as via the central bore 126 and/or the threaded holes 129.

Figure 5:
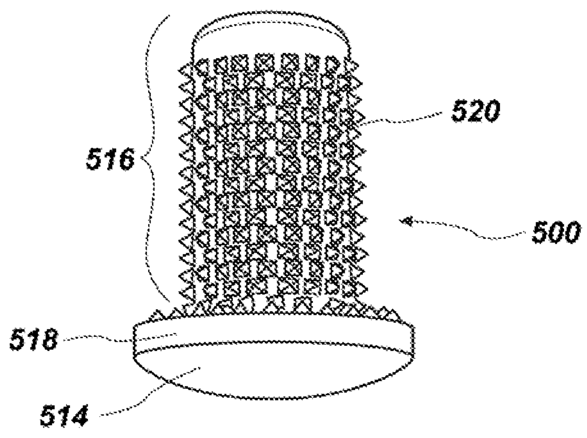
FIG. 5 illustrates an elongated bone cap having protrusions along an entire surface of the stem in accordance with one example.

Other modifications to the above described bone cap and method of installing a bone cap are also considered. For example, FIG. 5 illustrates an elongated bone cap 500. The elongated bone cap 500 can be similar to the bone cap 100 described above in many aspects. In this example, the elongated bone cap 500 can have engaging protrusions 520 that extend along an entire outer surface of the insertion extension portion 516. In some examples, the elongated bone cap 500 can also have engagement protrusions along a flange 518 of the proximal base 514.

Figure 6:
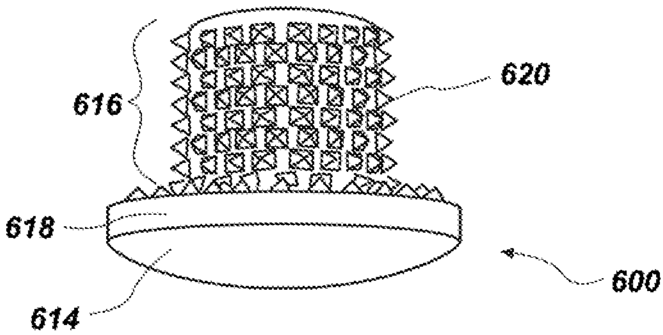
FIG. 6 illustrates a compact bone cap having protrusions along an entire surface of the stem in accordance with one example.

In another example as shown in FIG. 6, a compact bone cap 600 can be provided. The compact bone cap 600 can be similar to the elongated bone cap 500 in that the compact bone cap 600 can have engaging protrusions 620 that extend along an entire outer surface of the insertion extension portion 616. In some examples, the compact bone cap 600 can also have engagement protrusions along a flange 618 of the proximal base 614.

Figure 7:
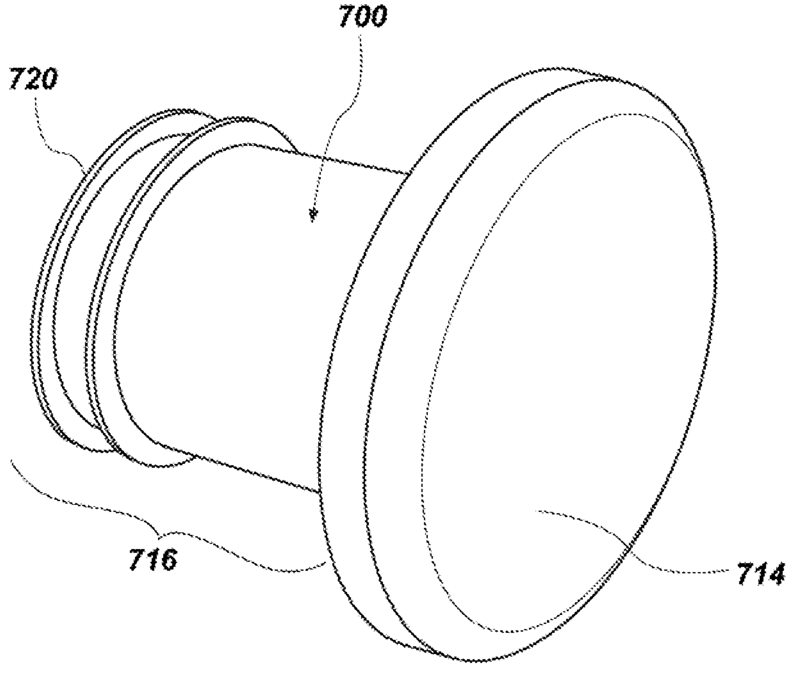
FIG. 7 illustrates a compact bone cap having a set of flanges as protrusions on a distal end of the bone cap in accordance with one example.

As discussed previously, the engaging protrusions can take on a variety of different shapes. FIG. 7 illustrates a bone cap 700. In this example, the bone cap 700 comprises engagement protrusions as circumferential flanges 720 that can be used to engage the bone. The circumferential flanges are disposed towards a distal end of the insertion extension portion 716 opposite the proximal base 714. Although two flanges are illustrated, as a general guideline, from two to about six flanges can be effective depending on flange width and materials used to form the flanges.

In another alternative, the proximal base includes an insertion tool engagement feature. For example, a hexagonal opening can be placed within the proximal base facing outward to allow engagement of an Allen wrench to facilitate insertion of the bone cap into the bone canal. Other tool engagement features can also be used such as, but not limited to, threaded recesses, detent recesses, and the like. In another alternative, the tool engagement feature can also be coupled to an expansion member to cause the proximal base, the insertion extension portion, or both to expand. Such expansion can allow for engagement with an inner surface of the bone after insertion of the bone cap. The expansion member can be formed of any suitable mechanism such as, but not limited to, expansion wedges (e.g. like drywall and concrete anchors), and the like.

Reference was made to the examples illustrated in the drawings and specific language was used herein to describe the same. It will nevertheless be understood that no limitation of the scope of the technology is thereby intended. Alterations and further modifications of the features illustrated herein and additional applications of the examples as illustrated herein are to be considered within the scope of the description.

Furthermore, the described features, structures, or characteristics may be combined in any suitable manner in one or more examples. In the preceding description, numerous specific details were provided, such as examples of various configurations to provide a thorough understanding of examples of the described technology. It will be recognized, however, that the technology may be practiced without one or more of the specific details, or with other methods, components, devices, etc. In other instances, well-known structures or operations are not shown or described in detail to avoid obscuring aspects of the technology.

Although the subject matter has been described in language specific to structural features and/or operations, it is to be understood that the subject matter defined in the appended claims is not necessarily limited to the specific features and operations described above. Rather, the specific features and acts described above are disclosed as example forms of implementing the claims. Numerous modifications and alternative arrangements may be devised without departing from the spirit and scope of the described technology.

What is claimed is:

1. A bone cap for reducing leakage of medullary canal components in a residual limb, comprising:

a proximal base;

an insertion extension portion extending from the proximal base, the insertion extension portion having an outer surface and a distal end opposite the proximal base, and the insertion extension portion being configured to be inserted into a resected portion of a bone of patient;

at least one bone engaging features disposed on the outer surface of the insertion extension portion adjacent to the distal end of the insertion extension portion, wherein the at least one bone engaging feature comprises a plurality of bone engaging features disposed in an array about the distal end of the insertion extension portion, and the array of bone engaging features comprises two or more rows of bone engaging protrusions; and a porous coating disposed on the outer surface of the insertion extension portion adjacent to the proximal base.

2. The bone cap of claim 1, wherein a top of the at least one bone engaging feature is a protrusion.

3. The bone cap of claim 2, wherein the protrusion is disposed on the outer surface of the insertion extension portion culminates in a sharp point, barbed component, angled flange, and/or fluted ribs.

4. The bone cap of claim 2, wherein the at least one bone engaging protrusion has a pyramid shape.

5. The bone cap of claim 2, wherein the at least one bone engaging protrusion has one or more of a conical shape, a flange shape, a barbed shape, an angled flange, and a fluted rib shape.

6. The bone cap of claim 1, wherein the at least one bone engaging feature is a cavity.

7. The bone cap of claim 1, wherein the bone engaging protrusions in a first row of the two or more rows of bone engaging protrusions are offset from an adjacent row of the two or more rows of bone engaging protrusions.

8. The bone cap of claim 7, wherein the porous coating is disposed on the annular flange.

9. The bone cap of claim 8, wherein the one or more apertures further comprises a plurality of screw holes disposed outside of the central bore.

10. The bone cap of claim 1 wherein the insertion extension portion from the proximal base to the distal end comprises a frustoconical structure.

11. The bone cap of claim 1, wherein the proximal base comprises an annular flange extending from a proximal side of the frustoconical structure.

12. The bone cap of claim 11, wherein the one or more apertures comprises a central bore.

13. The bone cap of claim 12, wherein the prosthetic is removably attachable to the central bore and the plurality of screw holes.

14. The bone cap of claim 1, wherein one or more apertures are formed in the proximal base.

15. The bone cap of claim 14, wherein the central bore is operable to receive a prosthetic, and the plurality of screw holes are operable to secure the prosthetic to the bone cap.

16. The bone cap of claim 1, further comprising a supplemental coating disposed on the outer surface, said supplemental coating being one or more of growth factors and antimicrobial coatings.

17. A method of installing a bone cap into a bone of a patient, the method comprising:

resecting an end of the bone of the patient to form a resection; and inserting the bone cap into the resection, the bone cap comprising:

a proximal base;

an insertion extension portion extending from the proximal base, the insertion extension portion having an outer surface and a distal end opposite the proximal base;

at least one bone engaging feature disposed on the outer surface of the insertion extension portion adjacent to the distal end of the insertion extension portion, wherein the at least one bone engaging feature is at least one of a protrusion and a cavity, wherein the at least one bone engaging feature comprises a plurality of bone engaging features disposed in an array about the distal end of the insertion extension portion, and the array of bone engaging features comprises two or more rows of bone engaging protrusions; and a porous coating disposed on the outer surface of the insertion extension portion adjacent to the proximal base; and engaging the at least one engaging feature with the resection to securely lodge the bone cap within the resection.

18. The method of claim 17, further comprising monitoring bone ingrowth into the porous coating.

19. The method of claim 17, wherein the bone engaging protrusions in a first row of the two or more rows of bone engaging protrusions are offset from an adjacent row of the two or more rows of bone engaging protrusions.

* * * * *